(12) United States Patent
Yancey et al.

(10) Patent No.: US 7,001,020 B2
(45) Date of Patent: Feb. 21, 2006

(54) COMPLETE AUTOREFRACTOR SYSTEM IN AN ULTRA-COMPACT PACKAGE

(75) Inventors: Don R. Yancey, Honolulu, CA (US); Leonard Schupak, Mission Viejo, CA (US); Charles E. Campbell, Berkeley, CA (US)

(73) Assignee: Daphne Instruments, Inc., Honolulu, HI (US)

( * ) Notice: Subject to any disclaimer, the term of this patent is extended or adjusted under 35 U.S.C. 154(b) by 284 days.

(21) Appl. No.: 10/207,412

(22) Filed: Jul. 26, 2002

(65) Prior Publication Data

US 2003/0025877 A1    Feb. 6, 2003

Related U.S. Application Data

(60) Provisional application No. 60/309,288, filed on Aug. 2, 2001.

(51) Int. Cl.
*A61B 3/10*        (2006.01)
*A61B 3/00*        (2006.01)

(52) U.S. Cl. .................. 351/221; 351/205; 351/211; 351/246

(58) Field of Classification Search ............... 351/200, 351/205, 206, 208–216, 218, 221, 246; 235/454, 235/462.06, 462.18, 462.24; 250/227.24, 250/227.32; 385/43
See application file for complete search history.

(56) References Cited

U.S. PATENT DOCUMENTS

| 3,843,240 | A | * | 10/1974 | Cornsweet | 351/211 |
|---|---|---|---|---|---|
| 4,715,703 | A | * | 12/1987 | Cornsweet et al. | 351/205 |
| 4,856,891 | A | * | 8/1989 | Pflibsen et al. | 351/210 |
| 5,192,863 | A | * | 3/1993 | Kavehrad et al. | 250/227.24 |
| 5,625,428 | A | * | 4/1997 | Isogai | 351/208 |
| 5,684,561 | A | * | 11/1997 | Yancey | 351/209 |
| 6,386,452 | B1 | * | 5/2002 | Kawamura | 235/454 |
| 6,471,637 | B1 | * | 10/2002 | Green et al. | 600/109 |
| 6,511,180 | B1 | * | 1/2003 | Guirao et al. | 351/211 |
| 6,561,648 | B1 | * | 5/2003 | Thomas | 351/221 |
| 6,623,117 | B1 | * | 9/2003 | Shibutani et al. | 351/211 |
| 6,685,318 | B1 | * | 2/2004 | Kohayakawa | 351/208 |

* cited by examiner

*Primary Examiner*—Eleni Mantis-Mercader
*Assistant Examiner*—John R. Sanders
(74) *Attorney, Agent, or Firm*—Gordon & Rees LLP

(57) ABSTRACT

An autorefractor system in an ultra-compact package is described for rapidly and objectively measuring the refractive state of the eye. The autorefractor detector system, in conjunction with a secondary light source, uses one photodetector such as a charge coupled device ("CCD") or one photodiode, to intercept a light beam at two distances from a secondary retinal light source created by one relay lens, one pupil emitter conjugate lens and one pupil detector conjugate lens. The signals produced by the photodetector are used to determine the full spherocylindrical refraction of the eye. A novel illumination and imaging system provides multiple capabilities to image the eye, control accommodation, and acquire and maintain optical alignment, while obtaining other measurements of the eye.

40 Claims, 9 Drawing Sheets

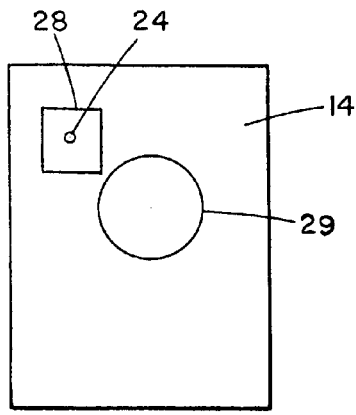
FIG. 1B
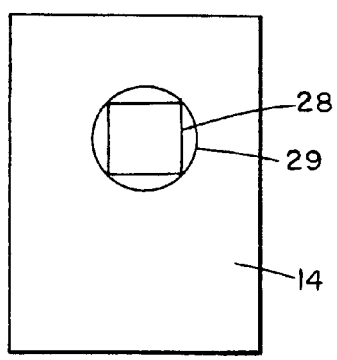
FIG. 1C
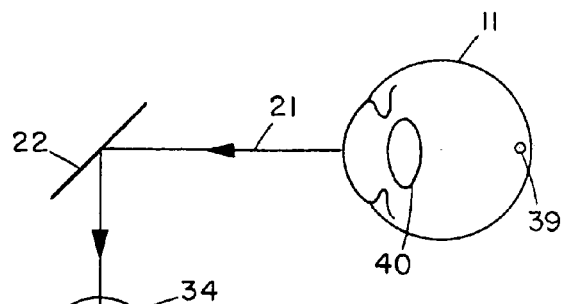
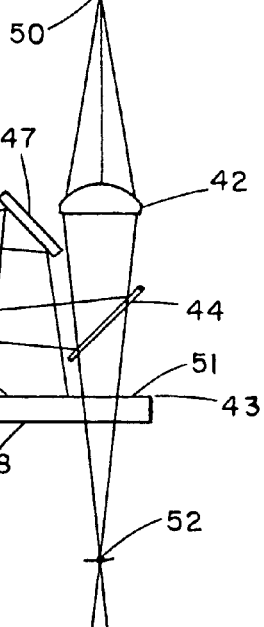
FIG. 2

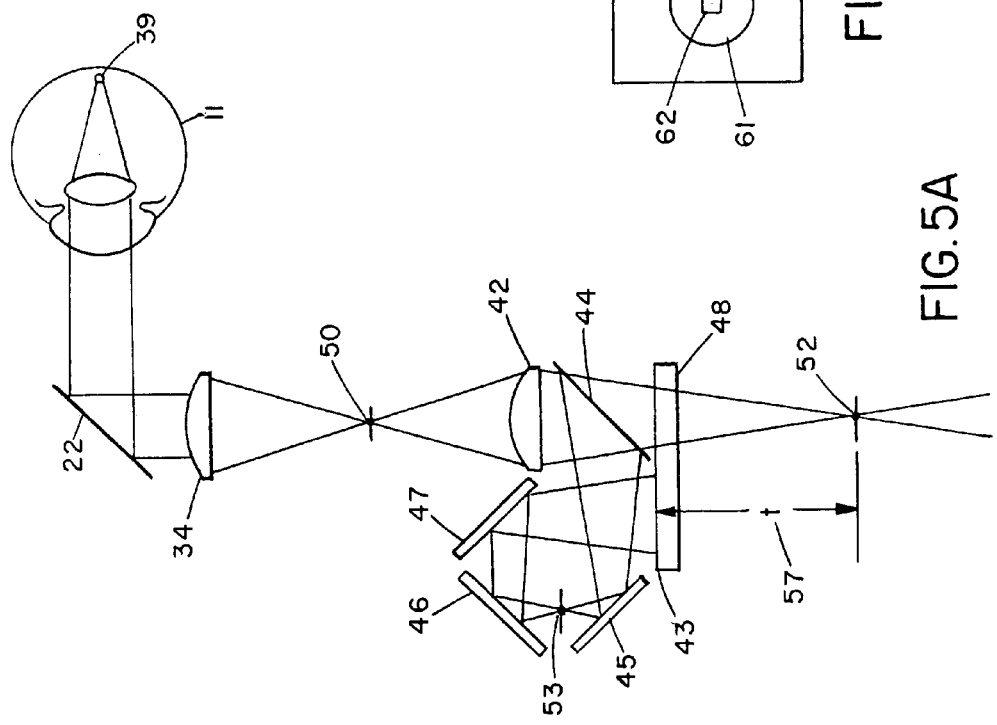
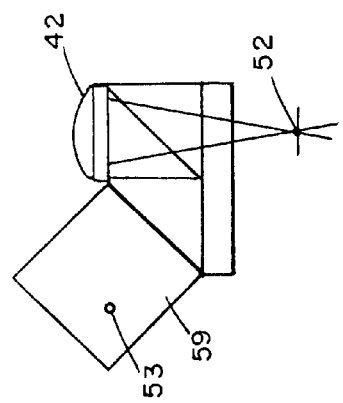
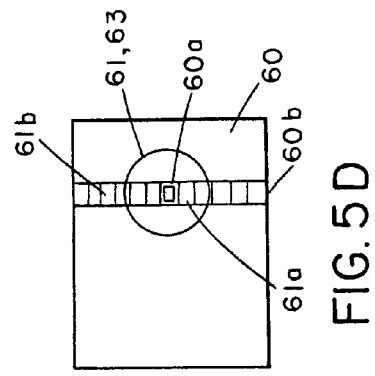
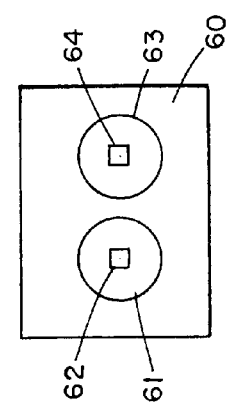
FIG.5A
FIG.5B
FIG.5C
FIG.5D

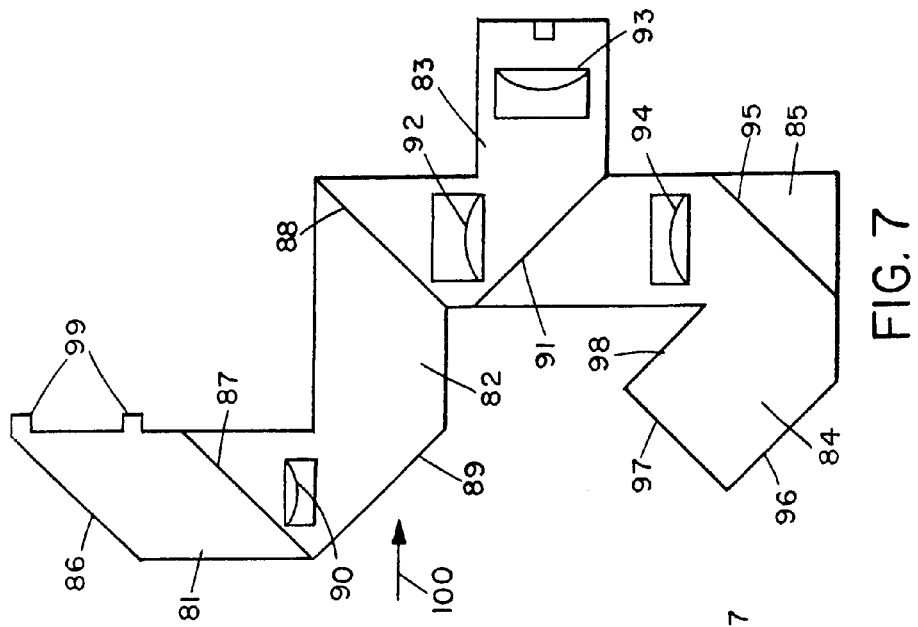
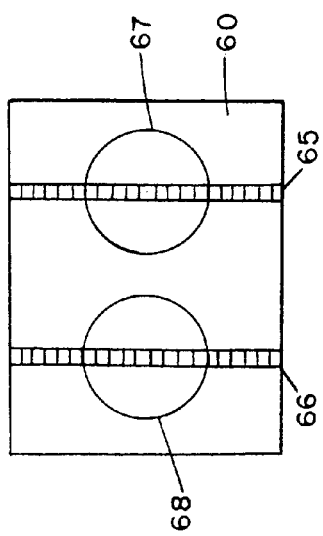
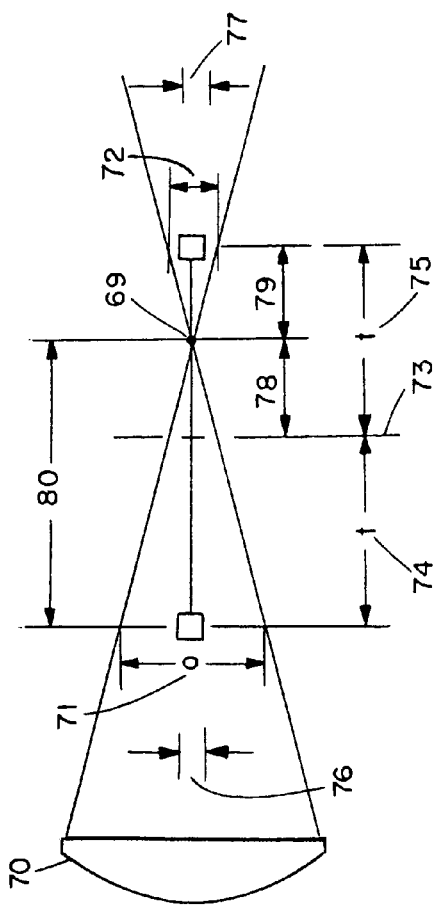

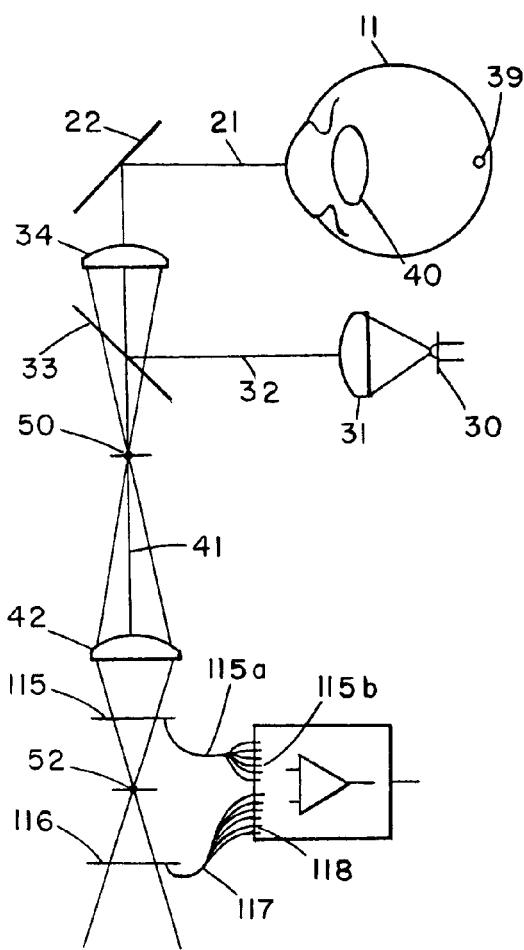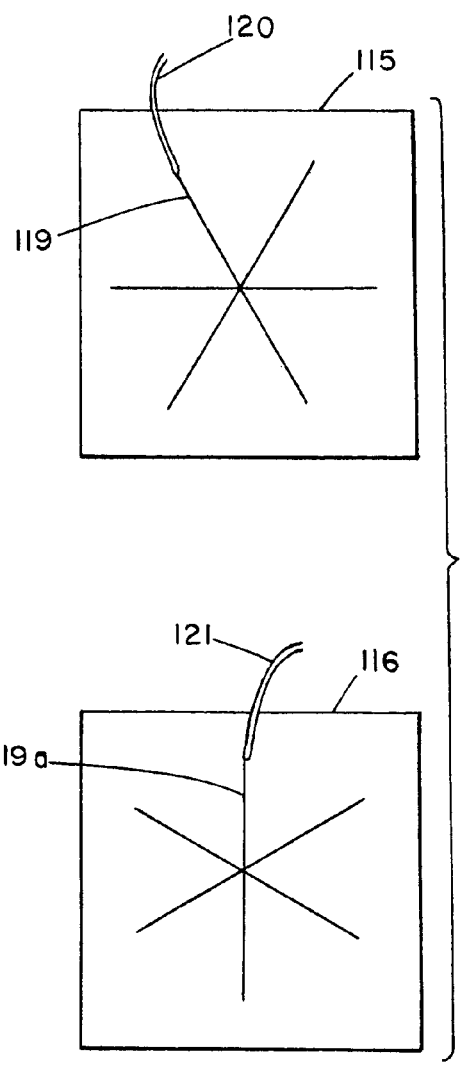
FIG. 9A
FIG. 9B

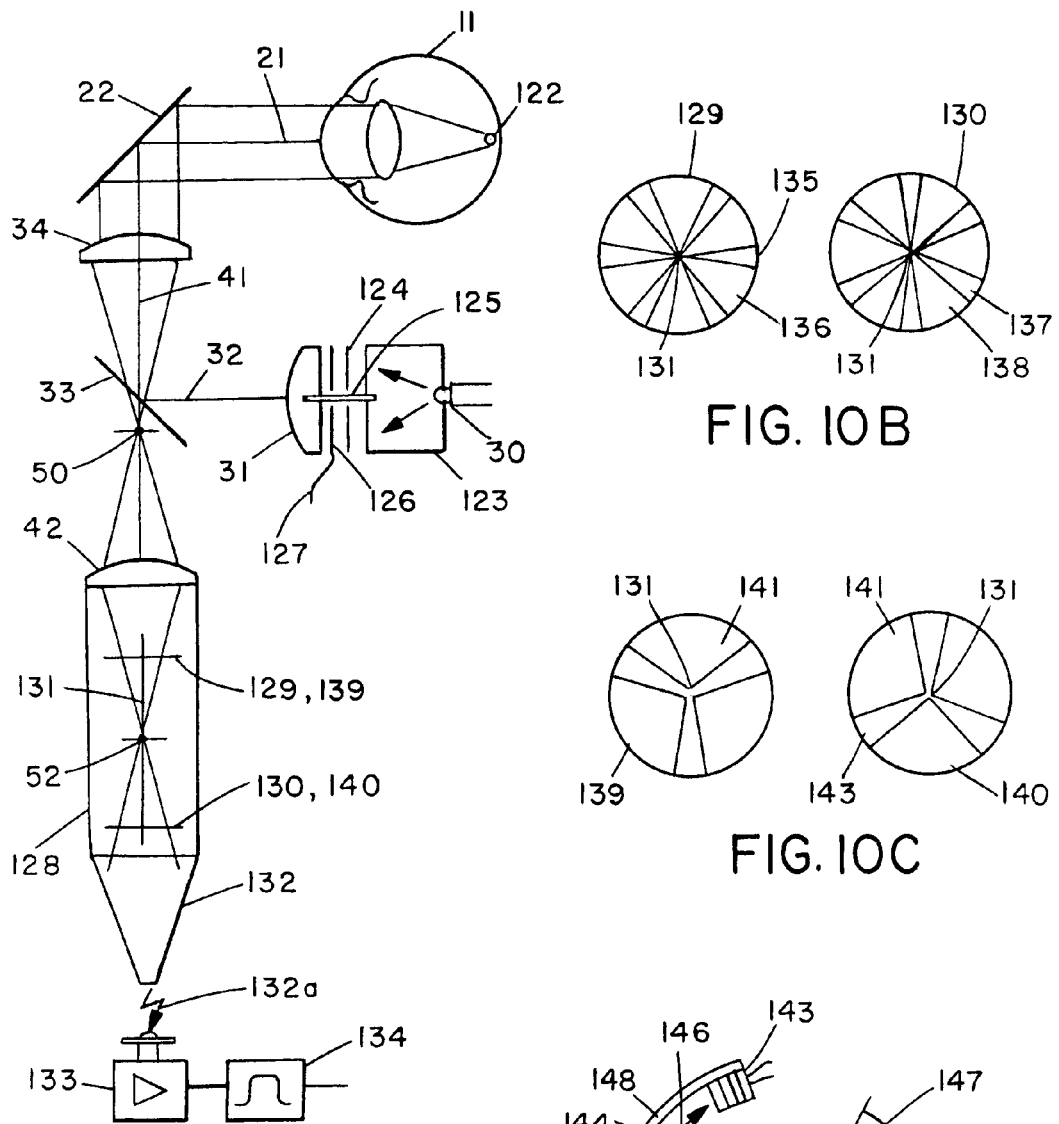
FIG. 10A
FIG. 10B
FIG. 10C
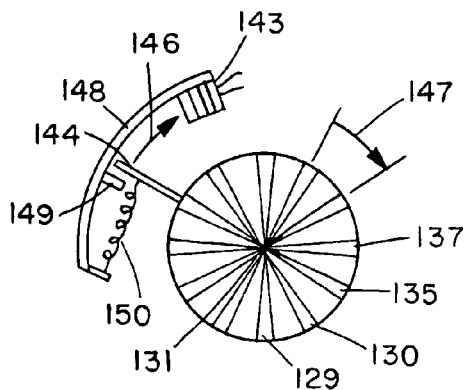
FIG. 10D

COMPLETE AUTOREFRACTOR SYSTEM IN AN ULTRA-COMPACT PACKAGE

CROSS-REFERENCE TO RELATED APPLICATION

This application claims priority from Provisional Patent Application Ser. No. 60/309,288 filed on Aug. 2, 2001.

BACKGROUND OF THE INVENTION

1. Field of the Invention

This invention relates to optical instruments for measuring refraction of the eye and of lenses and specifically to an instrument for rapid objective refraction.

2. Description of the Prior Art

Machines to automatically and objectively measure the optics of the eye are essential for eye care, yet these machines, called "autorefractors," are of limited use. Complexity and high price limit the use of these essential machines to perhaps less than 1% of the world's peoples.

Complexity and high prices also means these machines are used mostly in the advanced, industrial nations. Even in these rich nations, however, large populations are not reached. This includes patients of family physicians, children treated by pediatricians, and students in schools. Family physicians, pediatricians, and schools are unable to afford the high prices of these complex machines.

Most affected are children. In the U.S. an estimated one out of every 20 preschool children has a vision problem, which, if undetected and uncorrected, will affect the child's education and development. Another problem is amblyopia ("dull eye"). Vision in one eye is suppressed, and, if untreated, the child becomes blind in that eye. An estimated 3% of children in the U.S. have amblyopia. Amblyopia must be detected and treated at an early age to prevent blindness.

Adults are affected, too. Much of the world has limited eye care. In large parts of the world many people are vision impaired. Some are almost blind. For many their problem is simply poor refractive vision. The solution is autorefraction and corrective lenses. Our autorefractor provides a way to help solve these vision problems, such that people with poor refractive vision can be restored to useful, productive lives.

Conventional autorefractors typically measure how light rays are bent or "refracted." Another method (Yancey, U.S. Pat. Nos. 5,329,322 and 5,684,561) used measurement of intensity of light. Yancey, however, neither described a method nor showed an embodiment for achieving full refraction of the eye. Full refraction is "spherocylindrical" and in addition to sphere correction must also include cylinder and axis measurements. Yancey describes a method of "foci", which requires at least three lenses (a pupil lens and two other lenses acting as small telescopes) to look at areas ("foci") in different areas of the eye. Yancey requires at least two detectors, and these two detectors must operate in at least two independent optical paths.

To be practical, an autorefractor must have a means of optically aligning the optics of the instrument with the optics of the eye. Additionally, where the eye is looking and focused must be controlled. Where the eye is looking and focused refers to "accommodation." Accommodation refers to compression and change in the eye lens so as to focus on a nearby object. Conventionally, refraction requires that the eye be looking at a distant target. This target is usually at a standard distance of 20 feet (or five meters). Accommodation, focusing on a nearby object, would cause refraction of the eye to be in error. Therefore, accommodation must be controlled.

Conventional stand-mounted autorefractors typically use a series of sensors and motors to acquire the eye. Another system of sensors and motors is used for fine optical alignment. Still another, third, system of optics and motors is used to control where the eye is looking and focused. These systems are complex, bulky, and expensive.

SUMMARY OF THE INVENTION

Our invention is designed to provide hitherto unavailable eye care to large populations in vast geographic regions. Additionally, our invention, unlike others, is ultra-compact and easy to use. Our handheld autorefractor is about the size of a standard ophthalmoscope and used similarly. Anyone who can use an ophthalmoscope will find our invention exceedingly easy to use.

Our invention is a complete autorefractor system in an ultra-compact package. Unique methods and embodiments enable our autorefractor to rapidly and objectively measure the refractive state of the eye. The autorefractor detector system, in conjunction with a secondary light source, uses one photodetector such as a charge coupled device ("CCD") or one photodiode, to detect changes in a light beam at two distances from a second retinal image created by one relay lens and one pupil conjugate lens. The signals produced by the photodetector are used to determine the full spherocylindrical refraction of the eye. A novel illumination and imaging system provides multiple capabilities to image the eye, control accommodation, and acquire and maintain optical alignment, while obtaining other measurements of the eye.

Various embodiments use static light, or spatially modulated light, to measure the refraction of distinct areas of the eye as well as refraction of meridians to obtain spherocylindrical measurement. An alternative embodiment employs only one low-cost photodiode in the detector path.

Our method creates a retinal light source, which is analyzed at different distances using a very simple system of only two lenses and one detector. Creating a second retinal image requires one relay lens which forms the first retinal image, and one pupil conjugate lens which forms the second retinal image. That is, the detector requires a total of only two lenses. After creation of the second retinal image the method then intercepts and measures areas of the second retinal image beam intensity at different distances from the second retinal image. Our method requires only one detector. Moreover, the detector path requires only one relay lens and only one pupil conjugate lens, which operate together in a single path formed by the relay lens and the pupil conjugate lens.

It is essential that any practical autorefractor measure the spherocylindrical refraction of the eye. Our invention fully describes unique methods and embodiment to obtain full, spherocylindrical refraction of the eye. The prior art system of Yancey does not. As the reader will appreciate, other differences and additional advantages of our method and embodiment will become apparent in this description of our complete autorefractor system in an ultra-compact package.

The system also allows measuring curvature of the cornea (the cornea is the outer, clear covering of the eye), i.e., keratometry. To incorporate a keratometer means simply adding light sources to be reflected from the cornea so that changes in the positions of the reflected light sources can be detected and measured. This is a standard technique well known in the art. With appropriate lenses, substituted for the simple lens shown, the retina and other structures of the eye can be imaged.

Therefore, in one embodiment the invention is directed to apparatus for obtaining spherocylinder measurement of an eye comprising a primary emitter of a light beam having one emitter pupil conjugate lens and one relay lens to form a secondary retinal light source from the light beam on the eye's retina; a photodetector comprising a light detector for measurement of at least a first retinal image and a second retinal image of the secondary retina light source as observed by the photodetector respectively at distal and proximal positions relative to the secondary retinal light source and generation of signals proportional to the measured images, and computation means responsive to the signals for calculating the spherocylinder measurement of the eye. In further embodiments the apparatus is further defined by the photodetector comprising a detector pupil conjugate lens and/or a beam splitter and a mirror assembly.

In yet another embodiment the invention is directed to a method for obtaining spherocylinder measurement of an eye comprising creating an optical light path by causing a primary emitter of a light beam having one emitter pupil conjugate lens and one relay lens to form a secondary retinal light source from the light beam on the eye's retina; disposing a photodetector comprising a light detector in the optical light path for measurement of at least a first retinal image and a second retinal image of the secondary retina light source as observed by the photodetector respectively at distal and proximal positions relative to the secondary retinal light source and generation of signals proportional to the measured images, and calculating from the signals the spherocylinder measurement of the eye. In further embodiments the optical properties of the eye modify and direct light rays in the optical light path such that the luminous irradiance comprising pixels impinging on the photodetector varies in response to the optical properties of the eye and/or the method further comprises from the measurement determining a correct prescription for the adjustment of the eye to emmetropic vision.

BRIEF DESCRIPTION OF THE DRAWINGS

In the drawings, closely related figures have the same number but different alphabetic suffixes.

FIGS. 1A–1C show the preferred embodiment with the main optical components and layout of the complete autorefractor system.

FIG. 2 shows the detector system, comprising a relay lens, a pupil conjugate lens, a beam splitter with mirror assembly and one CCD detector.

FIG. 5A shows the preferred embodiment of a detector system illustrating one relay lens forming a first retinal image and one pupil conjugate lens forming second retinal images, and a single CCD detector; FIG. 5B shows a solid embodiment of a detector system pupil conjugate lens with a single CCD detector to obtain information about refractive error; FIG. 5C shows the view on the detector system CCD face and FIG. 5D shows a view of the CCD detector face for determining beam diameter.

FIG. 6A shows a view on the detector system CCD face illustrating near and far beam cross sections with rows of individual pixels representing meridians and FIG. 6B shows the geometry created by utilizing rows of individual pixels to obtain meridional power in various meridians.

FIG. 7 shows the preferred solid-path optics of the complete autorefractor system, comprising five optically transparent blocks.

FIGS. 9A–9B show a second preferred embodiment, which is a distinctly different refractor system comprising an eye, optics, emitter, and detector.

FIGS. 10–10D show a third preferred embodiment, a distinctly different and unique embodiment, which comprises the eye, optics, emitter with spatially modulated light, fixed and staggered opaque meridians, and single photo diode detector.

DETAILED DESCRIPTION AND PREFERRED EMBODIMENTS

Figure 1A:
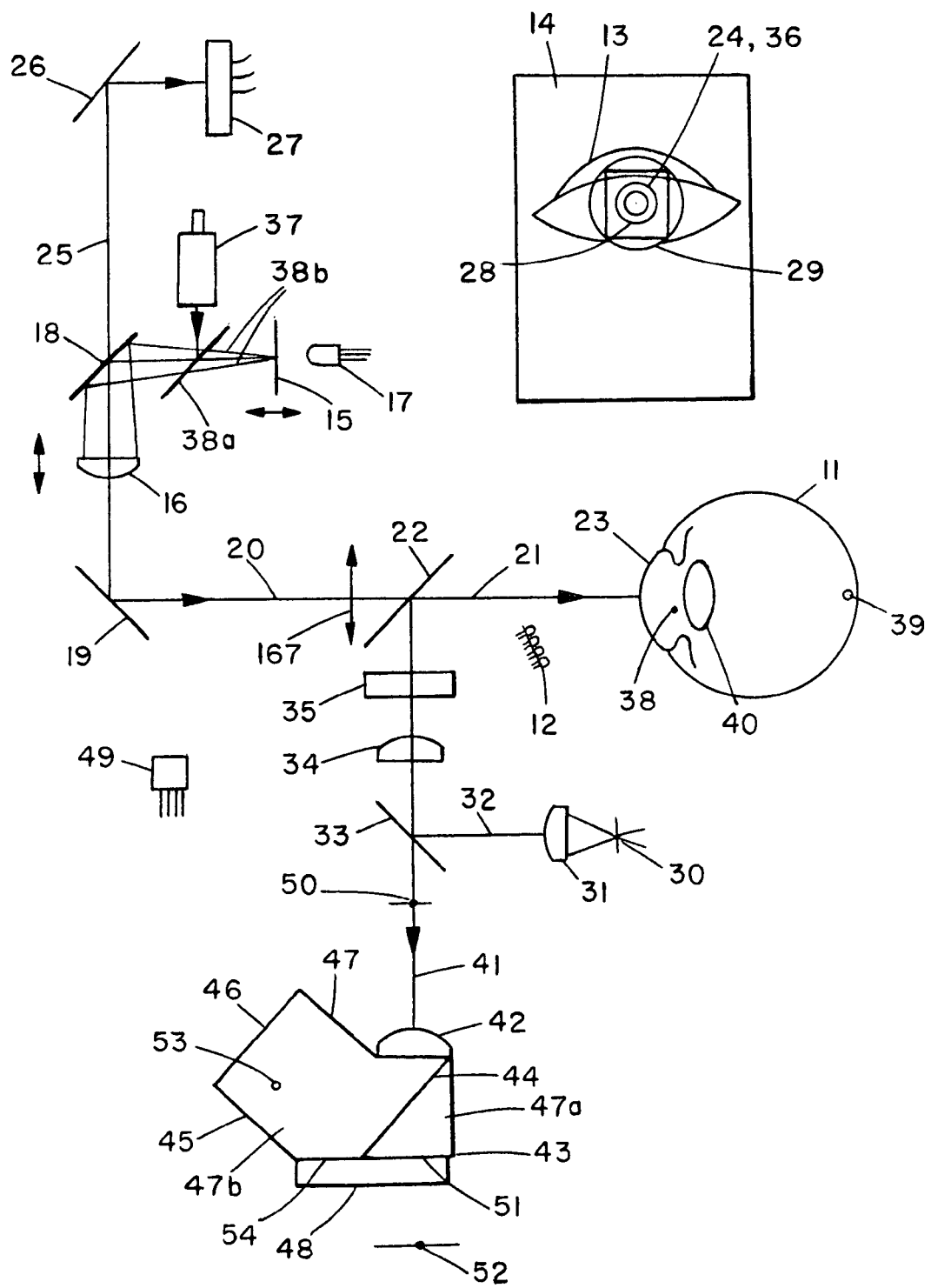

Our invention uses a simple yet novel embodiment for optical alignment. This novel embodiment also controls where the eye is looking and focused. In conjunction with sources to illuminate the eye and a CCD to image the eye, the basic embodiment comprises one lens and one beam splitter. This simple system provides multiple capabilities.

First, our illumination and imaging system provides a fixation target. The fixation target, at infinity, is looked at, "fixated," by the patient. On an LCD screen the system simultaneously images the eye to facilitate locating and acquiring the eye. A series of color prompts and guide marks on the LCD make alignment easy. Using the LCD screen, the operator simply moves an illuminated square into the center of a fixed illuminated circle. Reflections from the cornea of the eye are sensed by the CCD imager. These reflections are caused by the refractor emitter and by the fixation target. The reflections are made to coincide by a simple beam steering plate to achieve fine alignment automatically. The operator need only make the initial alignment to within a few millimeters. Because the image of the eye on the LCD is enlarged about two times, alignment is easily achieved even by inexperienced operators.

The system of illumination includes three LEDs illuminated in sequence, about one-thirtieth of a second each. The LEDs are red, green, and blue. A fourth LED, invisible infrared (IR) light, is for supplemental illumination of the eye. The three color LEDs, red, green, blue, provide full-color illumination of the exterior of the eye. The IR LED provides non-visible illumination for dim lighting conditions.

For full color imaging of the fundus (back) of the eye only two colors are required, red and green. The fundus does not reflect blue. Our method and embodiment is a low-cost way to achieve full color with a monochrome CCD because color-emitting LEDs illuminated sequentially are used.

Moreover, compared to single-chip color CCDs, resolution is higher because the monochrome CCD does not use color masks as are employed in color CCDs. Further, compared to a conventional high resolution three-chip color CCD, our full-color single chip is more compact.

In conjunction with keratometer and refractive measurements, structures of the eye and features on the retina such as the optic disc can be dimensioned. Such dimensions mean retinal images can be scaled to size. Scaling to size enables one-to-one comparison with otherwise disparate retinal images. Using a library of retinal images, or standardized data, one-to-one comparison facilitates image analysis. Consequently, this facilitates diagnosis of eye disease.

With the simple lens, the exterior of the eye can be imaged and the pupil diameter can be measured and recorded. Whether the pupil is small (eye accommodating) or the pupil is large (eye not accommodating), determines which refractive measurements are used or not used. This improves measurement accuracy. An additional benefit of measuring pupil response is neurological. For example, using light stimuli and observing the presence or absence of pupil response assists in diagnosis of tumors and head trauma.

The fixation target can be varied in focus for standard fogging of the eye, and then put into focus for myopic or hyperopic eyes for additional refractive measurements. Instead of using the fixation target to control accommodation, an illuminated pinhole can be projected into the pupil of the eye. This illuminated pinhole immediately causes relaxation of the eye lens.

The capabilities of the illumination and imaging system enable more accurate refraction of the eye. These capabilities include 1) fixation target, variable in optical focus, 2) illuminated pinhole target, 3) measurement of pupil size (a pupillometer), 4) imaging of eye for initial alignment, 5) corneal reflections sensor for auto fine alignment, 6) determine vertex distance, 7) measure curvature of cornea (keratometry), 8) image external and internal structures of the eye for image analysis and to assist disease diagnosis, and 9) full-color imaging of the eye with a low-cost monochrome CCD.

Because our method requires only a minimal number of parts, our complete autorefractor is aptly characterized by its simplicity. Entirely self contained and battery powered, all components fit in an ultra-compact package. Components include electronics and optoelectronics. Signal processing is relatively low cost. The major cost is the optics. Our invention uses solid-path optics. This means the optics are integrated as a solid block of glass, or plastic, with air surfaces acting to reflect and refract light. Instead of imaging, our invention mostly uses illumination. This decreases the need for precision alignment and super-flat surfaces. Further, the non-critical nature of our solid-path optics facilitates mass manufacturing and cuts cost.

Moreover, path length is reduced by the reciprocal of the index of refraction. For an index of refraction of 1.6, optical path length is shortened by about 40%. Shortening the optical path reduces the already compact dimensions of our autorefractor. Solid-path optics, therefore, results in greater simplicity and lower cost.

Turning then to the drawings, FIGS. 1A–1C show the first preferred embodiment of the complete autorefractor system, illustrating optical layout and components. This includes illumination, control of accommodation, initial manual alignment using a color LCD, automatic fine tracking of the eye, and the refraction unit itself. The autorefractor system of FIG. 1A may be divided into four main sections. These sections are 1) illumination and control, 2) refractor unit, 3) solid-path optics, and 4) color LCD. These four sections operate together as a system. Using the principles described in these specifications, one skilled in the art can use a commonly available optics design program such as those commercially available under the trade names "ZEMAX" or "SIGMA 2000" to determine dimensions and placement of optics. Such dimensions and placement of optics depend on focal lengths of the relay lens and conjugate pupil lenses.

For purpose of illustration only, typical relay lens and conjugate lens are described here. The refractor may use focal lengths for a relay lens of 24 mm and conjugate pupil lens of 12 mm. Relay and conjugate lenses, such as Edmund Scientific Stock Nos. L45-471 and L32-965, respectively, are commercially available. Other lenses with different focal lengths may be used as will be appreciated by those skilled in the art.

In our invention as in other optical instruments for imaging and for measuring light intensities, reflections from lenses and other surfaces must be carefully controlled. Black mirrors, at 45° angles, are used to reflect unwanted light from beam splitters onto a black matte surface. These black mirrors, fabricated from black Lucite, attenuate unwanted light. Residual light in the system may be zeroed out electronically. Reflections from the cornea of the eye may be suppressed by circular polarizers or by opaque discs. Opaque discs, 1 mm in diameter, can be used to block paraxial reflections from the cornea and eye lens. These opaque discs are centered in 3.0 mm diameter stops. The 3.0 mm diameter stops are standard stops placed in front of refractor lenses, that is, on the side of the lens facing the eye being refracted.

In FIG. 1A, eye 11 is illuminated by LEDs 12, which eye image 13 appears on color LCD 14. Eye 11 sees target 15, set at optical infinity by lens 16 and illuminated by LED 17. Illumination by LED 17 through target 15 reflected by beam splitter 18 and focused at optical infinity by lens 16, is directed by mirror 19 along optical paths 20, 21 through movable beam splitter 22 to cornea 23. Illumination by LED 17 on cornea 23 produces a reflection, a first Purkinje image 24. Illumination is shown by light rays 38b transmitted through beam splitter 38a.

Image 24 is returned along optical paths 20, 21, and 25, reflected by mirror 26 into eye imager CCD 27. Distances of optical paths 20, 21, 25 are used to select lens 16 so that the first Purkinje image 24 is properly in focus on CCD 27. Image 24 detected by CCD 27 is converted by software to a movable illuminated square 28, which is centered on image 24. When eye 11 is stationary, square 28 is moved to the inside of fixed illuminated circle 29. Square 28 is moved by simply moving the instrument itself. Note that square 28 and circle 29 may be superimposed over a full-color or black-white image of eye image 13.

A second First Purkinje image 36 is generated by emitter 30 and emitter conjugate lens 31 along optical path 32, beam splitter 33, relay lens 34, beam splitter 22, along optical path 21, and on to cornea 23. Output of emitter 30 impinging on cornea 23 causes a second First Purkinje image 36. This second image 36 is similar to image 24, except that images 24 and 36 are temporally interleaved.

Image 36 is similarly detected in the manner of image 24 by CCD 27. Electronics and software compare the positions of images 36 and 24, that is, compare the positions of images 24, 36 on CCD 27, and then send electronic signals to an X-Y beam steerer 35 and, optionally, 22, to cause images 24 and 36 to coincide. In this case, "images 24 and 36 to coincide" means that the optics of the instrument are aligned with the optics of an eye being refracted. Beam steerer plate 35 is a plate of glass, about 6 mm in thickness, that is tilted in the X-axis to cause the optical path to change in a parallel manner, that is, steered in the plus or minus X-direction depending on how much the plate is tilted off perpendicular to the optical path. Similarly, by tilting the plate in the Y-axis, the optical path is thereby changed so that an impinging beam is accordingly steered in a plus or minus Y-direction. One plate may be used, or two separate plates at 90° orientation to each other, for X- and Y-axes, may be used. Plate 35 is used to track the eye and insure precision alignment of the invention's optics with the optics of the eye.

Target 15 may be moved to change optical focus of target 15 on cornea 23, and lens 16 may also be moved to change optical focus of target 15 on cornea 23. The resulting "in" and "out" of focus images, including eye image 13, detected by CCD 27 are used to determine vertex distance, that is, distance from instrument optics to an eye being refracted. This helps ensure that an eye being refracted is within proper measurement distance. This system is relatively insensitive to changes in vertex distance, which facilitates easy operation. Note, too, that eye image 13 is enlarged about two times actual size, which helps bring the instrument into proper vertex range intuitively. Moreover, fixed illumination circle 29 is approximately the size of an eye's cornea/iris, which further facilitates proper vertex distance location as well as initial manual alignment.

Target 15 can be moved in order to present to eye 11 a plus diopter target. A plus diopter target, known as "fogging," helps control accommodation. Generator 37 employs beam splitter 38a to place an illuminated pinhole in pupil 38. Alternately, illuminated pinhole generator 37 can be employed to relax accommodation. Eye imager CCD 27 also monitors and records diameter of pupil 38. Smaller diameters of pupil 38 indicated accommodation, while larger diameters of pupil 38 indicate relaxation of accommodation. Emitter 30 and emitter pupil conjugate lens 31 via optical path 32, as previously described, generates a First Purkinje Image. The primary purpose of emitter 30 and lens 31 is to put a spot of light, a secondary light source 39, on the retina of eye 11. The light from this secondary light source 39 exits the eye through eye lens 40 via optical path 21, reflected by beam splitter 22 through beam steerer plate 35 to relay lens 34, and along optical path 41, forming a first retinal image 50, and then to detector pupil conjugate lens 42. Lens 42 forms second retinal images 52, 53, in "front" and "behind" (or "above" and "below") detector plane 43 of CCD detector 48. CCD detector 48 then produces signals used to determine full spherocylindrical refraction of an eye 11. Accelerometer 49 detects and measures inclination of autorefractor system (FIG. 1A) with respect to eye 11, assuming that eye 11 is in a vertical, normal position. Signals from accelerometer 49 indicate amount of "tilt" of the autorefractor system of FIG. 1A from a vertical, normal position, and provides a corrective factor for "axis" measurement.

Another preferred embodiment uses a spatially modulated light source with a bandpass filter for the detector signals in order to eliminate unwanted light and extraneous signals.

As an example of this invention being operated as a system, beam steerer plate 35 is controlled by first section and associated electronics, but plate 35 is also part of second section refractor unit: Beam steerer plate 35 controls fine alignment for accurate refractive measurements. A second example, the first section eye imager CCD 27 images the eye for display on color LCD 14.

The second section is the refractor unit. This comprises an emitter unit and a detector unit. This emitter unit mainly comprises an emitter 30, emitter pupil conjugate lens 31 and beam splitter 33. The emitter, in common with the detector path, uses relay lens 34 and beam steerer plate 35. Relay lens 34 forms first retinal image 50. The second section detector unit can be seen to comprise relay lens 34, detector conjugate pupil lens 42, beam splitter 44, mirrors 45, 46, 47, and CCD detector 48. Lens 42 generates second retinal images 52 and 53, with near beam 51 and far beam 54 shown in detector plane 43. A separate part is accelerometer 49. Accelerometer 49 provides a corrective factor of instrument inclination for axis measurements.

The third section is solid path optics. Autorefractor optics maybe solid-path configuration. In FIG. 1A only part of the autorefractor is shown configured in solid-path optics. Solid-path optics is illustrated by blocks 47a and 47b. Block 47a combines detector conjugate pupil lens 42, beam splitter 44, and mirrors 45, 46, and 47 into one piece. This one piece, block 47a, may be produced by various means, including injection molded plastic. Block 47b, not strictly necessary, combines with block 47a to complete an optical path.

The fourth section is the color LCD. Color LCD 14 shows image of an acquired eye, enlarged about two times, eye image 13, and First Purkinje Images 24, 36. Images 24 and 36 are reflections from cornea 23 of eye 11. Superimposed on eye image 13 is movable illuminated square 28 inside fixed illuminated circle 29.

FIG. 1B shows movable illuminated square 28 and fixed illuminated circle 29 and corneal reflection 24 in viewing circle 14. Alternatively, if one considers only fixed circle 29 of FIG. 1 B, then for manual alignment the eye 11 (FIG. 1A), or some part of the eye, can be moved into circle 29. Moving the eye into circle 29 means moving the instrument so that the eye, or some structure of the eye, is moved into circle 29 to manually align the instrument's optics with the optics of the eye. In FIG. 1B, therefore, the eye is represented by moveable square 28, and moveable square 28, superimposed on a view of the eye, is generated by detecting a corneal reflection on CCD 27 of FIG. 1A, and software generates an illuminated square that is centered on square 28. Manually moving the instrument to cause eye 11 with square 28 to move into circle 29 therefore aligns the instrument optics with the optics of the eye.

FIG. 2 shows the preferred detector path embodiment, also showing eye 11, secondary light source 39, eye lens 40, optical path 21, and movable beam splitter 22. This embodiment mainly comprises two lenses, relay lens 34 and detector pupil conjugate lens 42. These two lenses operate together in single optical path 41. Relay lens 34 forms a first retinal image 50, and pupil conjugate lens 42, in conjunction with beam splitter 44 and mirrors 45, 56, 47, forms second retinal images 52, 53. FIG. 2 shows secondary light source 39, which is a spot of light on retina of eye 11. Second light source 39 exits eye 11 through eye lens 40 via optical path 21, reflected by beam splitter 22, through relay lens 34, along optical path 41, forming first retinal image 50, and then impinging on detector pupil conjugate lens 42. Lens 42, in conjunction with beam splitter 44 and mirrors 45, 46, 47, forms second retinal images 52, 53. Detector CCD 48 detects a cross section of near beam 51 and similarly detects a cross section of far beam 54. Cross sections of beams 51,53, fall onto same detector plane 43 of single detector CCD 48. Signals of CCD 48 are used to determine spherocylindrical refraction of eye 11.

Figure 3:
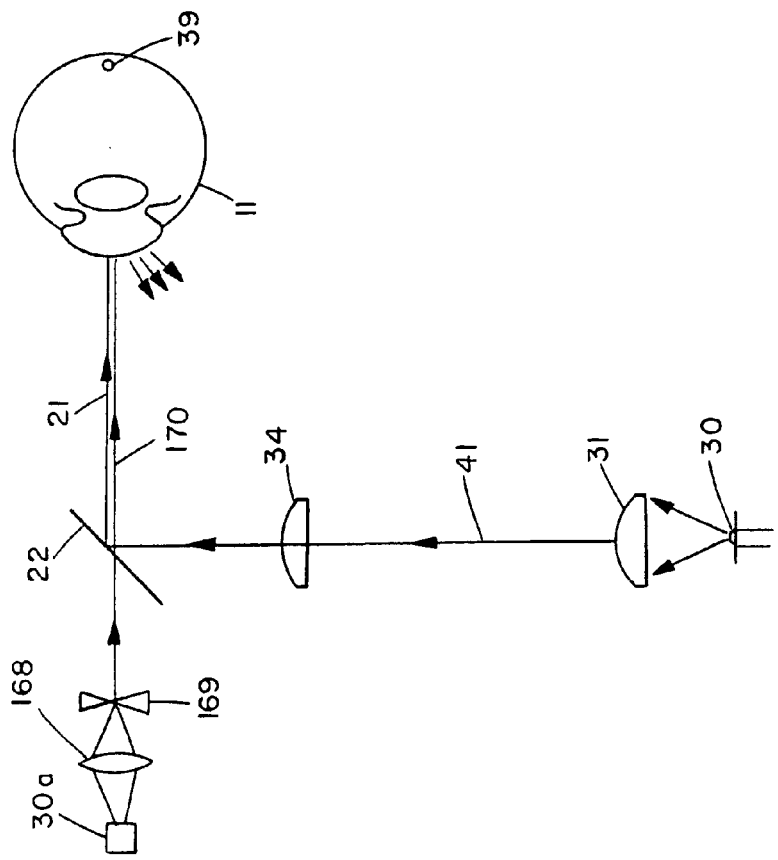
FIG. 3 shows the emitter system, partly unfolded, comprising an emitter, an emitter pupil conjugate lens, and a relay lens.

FIG. 3 shows the preferred embodiment of the emitter path, partly unfolded. Emitter 30, which may be an LED or other source of light emissions, in conjunction with emitter conjugate pupil lens 31 and relay lens 34, via optical path 41 and beam splitter 22 forms a secondary light source 39 on retina of eye 11.

Figure 4:
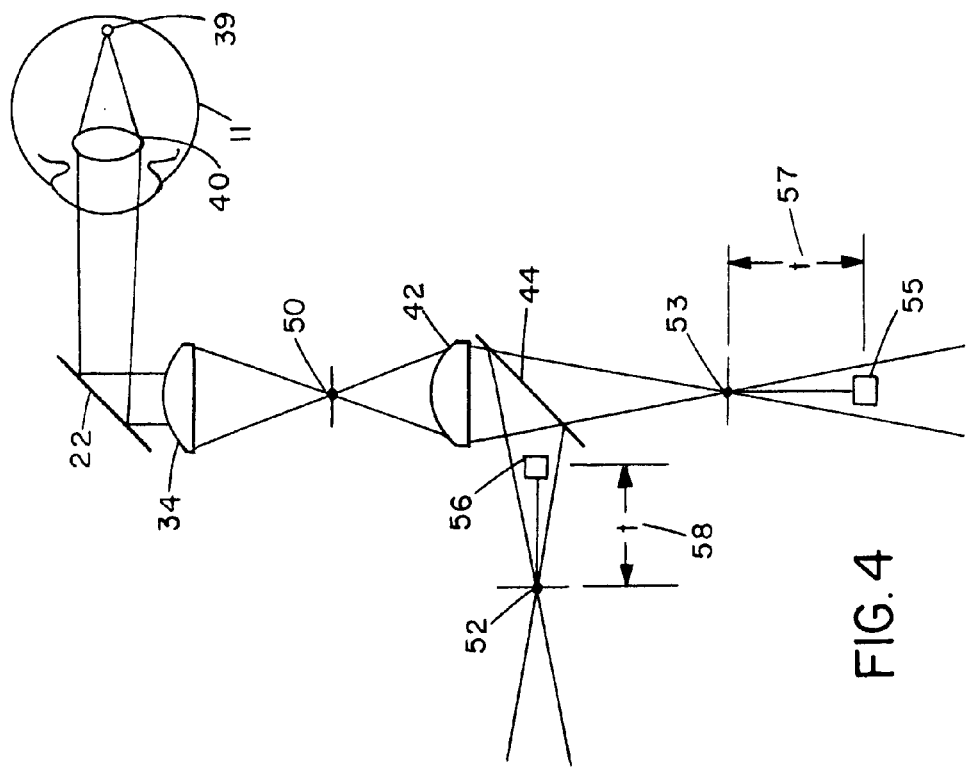
FIG. 4 shows one embodiment illustrating a relay lens forming a first retinal image and a pupil conjugate lens forming second retinal images, which are detected at near and far points from the second retinal images.

FIG. 4 shows one embodiment of the detector path. Secondary light source 39 on retina of eye 11 exits through eye lens 40 and via beam splitter 22 along optical path 41 to impinge on relay lens 34, creating first retinal image 50, and further impinging on detector pupil conjugate lens 42, which creates, via beam splitter 44, second retinal images 52, 53. Near detector 56 is located a distance t 58 from second retinal image 52, and far detector 55 is located a distance t 57 from second retinal image 53. In this Figure, distances t 57 and t 58 are shown as identical distances, although they can be the same or different distances. For the analyses presented herein t 57 and t 58 will be considered to be the same number of units of distance. It can be shown that if the distance of the detectors 55 and 56 from the second retinal image is equal and of value t (distance t 57, t 58), the difference of the two detector signals divided by their sum is equal to a function of mean refractive error M and the product of the maximum error times the minimum error K.

$$(S_1 - S_2)/(S_1 + S_2) = 2tM/(1 + 2tK) \quad [1]$$

This is roughly proportional to the mean error but gives no information about the astigmatic error.

FIGS. 5A, 5B, 5C, 5D show embodiments of the detector path which particularly relate to a solid-path device, FIG. 5B, and a CCD detector, FIGS. 5C–5D. In FIG. 5A, secondary light source 39 on retina of eye 11 exits eye 11, via beam splitter 22, and impinges on relay lens 34. Relay lens 34 forms a first retinal image 50, and then pupil conjugate lens 42, in conjunction with beam splitter 44 and mirrors 45, 46, 47, forms second retinal images 52 and 53. Second retinal images 52 and 53 fall a distance t 57 in "front" and the same distance t 57 "behind" CCD detector plane 43 of CCD detector 48. Dimensions of the device can be made so that second retinal images are located a known distance t 57 from detector plane 43 of detector 48. FIG. 5B shows monolithic block 59 with CCD detector 48. Block 59 incorporates pupil conjugate lens 42 and optics to produce second retinal images 52, 53. Fabricated separately and then adhered together to form monolithic block 59 are lens 42 and other components, beam splitter 44, and mirrors 45,46,47, described in FIG. 5A. Note that monolithic block 59 may be fabricated of, say, five separate pieces such as a lens, prisms and a cube. Block 59 may also be fabricated using only two separate pieces, blocks 47a, 47b, shown in FIG. 1A. Also shown are locations of second retinal images 52 shown outside block 59, and second retinal image 53 shown inside block 59. Detector CCD 48 is shown attached to block 59. FIG. 5C shows CCD detector face 60. Face 60 shows far beam diameter 61 overfilling representative pixel 62, and near beam diameter 63 overfilling representative pixel 64. FIG. 5D shows CCD detector face 60 and beam diameter 61 and 63. Diameters 61 and 63 are shown coinciding for illustrative purposes only. Representative center pixel 60a is the center of beam diameters 61,63. Pixel 60a may be determined empirically simply by using a model eye that is aligned with the optics and representative pixels row 60b. Then row 60b contains center pixel 60a. Representative inside pixel 61a and representative outside pixel 61b are used to determine beam diameters. That is, inside pixel 61a will have a higher intensity than outside pixel 61b. By comparing pixel 61a and 61b intensities, say, that 61a is a detectable level above background noise of pixel 61b, beam diameters 61 and 63 may be measured. Beam diameters 61,63, are then used in calculations to obtain refractions of meridians.

FIGS. 6A and 6B show embodiments of the detector path that obtain information for determining sphere, cylinder, and axis measurements of an eye and to obtain refraction of meridians. FIG. 6A shows CCD detector face 60 and cross sections of near beam 67 and far beam 68. Rows of individual pixels 65, 66, represent parallel meridians through the centers of cross sections of beams 67, 68, respectively. FIG. 6B shows a new geometry created by the analysis of FIG. 6A. FIG. 6B shows detector pupil conjugate lens 70 forming second retinal image 69, near beam $B_{near}$ 71, far beam $B_{far}$ 72, zero power plane 73 with distances t 74 and t 75, cross section size of pixels p 76, p 77 (both pixels, p 76, p 77, for this analysis are defined as having the same cross section size), distance $(1/-F_m)$ 78, distance $(1+(1/F_m))$ 79 and distance $(1-(1/F_m))$ 80. If we add rows of pixels 65, 66, parallel to one another, in each beam 67, 68, on CCD detector face 60, we sensitize the signal to meridional power in the refractive error. The amount of energy going through the two beam cross sections 67, 68, is equal. So if we added up all pixel values in beams 67, 68, the sums would be equal. But in a row of pixels, the dimensions of the row at right angle to its length is overfilled and so the difference in pixel value is sensitive to power in that direction. However, along the length of the row, the beam underfills the area and so is not sensitive to power in the long direction. Therefore, if we sum along two parallel diameters and call the sums $Sigma_1$ and $Sigma_2$, we find that $$(Sigma_1 - Sigma_2)/(Sigma_1 + Sigma_2) = 1/(tF_{meridian}) \quad [2]$$

$F_{meridian}$ is the power in the meridian at right angles to the row. We have essentially created a new geometry. In FIG. 6B a new geometry is illustrated. FIG. 6B shows second retinal image 69 created by detector pupil conjugate lens 70, near beam $B_{near}$ 71, far beam $B_{far}$ 72, zero power plane 73 with distances t 74 and t 75, cross section size of a pixel p 76, p 77, distance $(1/-F_m)$ 78, distance $(1+(1/F_m))$ 79, and distance $(1-(1/F_m))$ 80. By right triangles:

$$B_{near}/B_{far} = (t - (1/F_m))/(t + (1/F_m)) = (tF_m - 1)/(tF_m + 1) \quad [3]$$

$$Sigma_1 = p/B_{near} \quad [4]$$

$$Sigma_2 = p/B_{far} \quad [5]$$

$$(Sigma_1 - Sigma_2)/(Sigma_1 + Sigma_2) = \quad [6]$$
$$((p/B_{near}) - (p/B_{far}))/((p/B_{near}) + (p/B_{far})) =$$
$$((1 - (B_{near}/B_{far}))/((1 + B_{near}/B_{far})) =$$
$$(1 - ((tF_m - 1)/tF_m + 1)))/(1 + ((tF_m - 1)/tF_m + 1)))$$

and $$(Sigma_1 - Sigma_2)/(Sigma_1 + Sigma_2) = 2/2tF_m = 1/tF_m \quad [7]$$

By adding parallel pixel rows in different orientations to form sums $Sigma_1(theta)$, $Sigma_2(theta)$, the meridional power in various meridians, F(theta), can be found. At least three meridians are needed to obtain sphere, cylinder, and axis, but more can be taken for improved accuracy through multiple samples.

FIG. 7 shows a solid-path optics embodiment of the corresponding autorefractor system shown in FIG. 1A. FIG.

7 shows eye imager block 81 with mirror 86; illumination control block 82 with beam splitters 87, 88, mirror 89, and imaging lens 90; emitter block 83 with beam splitter 91, relay lens 92, and emitter pupil conjugate lens 93; first detector block 84, with detector pupil conjugate lens 94, beam splitter 95, and mirrors 96, 97, 98; and second detector block 85. Mounts 99 for optoelectronics components such as LEDs and CCDs, with standoff and threaded holes, may be integrally molded into the individual blocks. Individual blocks 81, 82, 83, 84, 85 are joined together into one monolithic block. The blocks are placed in a jig, optically aligned with each other, and then, using an adhesive, fixed into place.

Arrow 100 shows location of alternate or supplemental illumination and optics. In this case, mirror 89 becomes a beam splitter. Alternate or supplemental illumination and optics may include a CCD eye camera and illumination. This may also include accommodation control optics, illuminated targets for determining curvature of the cornea, and pupillometer.

The solid-path configuration shown, which might be described as a "Stretched S" or a "Zig-zag S", can be re-configured to other shapes. For example, blocks 81,82,83, and 84 and 85, may be rotated, re-arranged, and modified in numerous ways. One purpose to re-configure the arrangement shown in FIG. 7 may be to make the optics conform to a desirable instrument housing shape. Another purpose may be to add measurement functions. For example, by taking care to appropriately modify related optical components, block 81 or any one or more of other blocks 82,83,84 and 85, may be rotated, say, 90 degrees or 180 degrees, with respect to other blocks. Another example, an additional beam splitter can be inserted parallel to existing beam splitter 88. This additional beam splitter can be used for supplemental illumination or for incorporating an additional function such as keratometry.

Figure 8A:
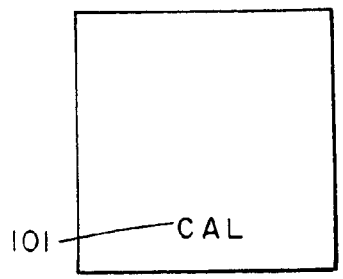
FIGS. 8A–8G show color LCD screens, each screen displaying prompts and guide marks to assist in easy step-by-step operation, that is, intuitive use.
Figure 8B:
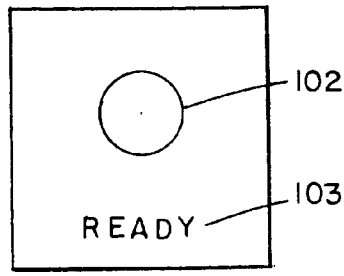

FIGS. 8A–8G show a series of color LCD screens with prompts and guide marks in symbols, colors and text to facilitate easy, intuitive use of the autorefractor. Indicated colors are preferred colors acting as prompts. Color prompts show operation status such as "blue" for "on", "green" for OK, and "red" for trouble. Prompts in "yellow" indicate action to be taken. If low battery, or other problem, then in screen of FIG. 8A appears, for example, "Low Battery" in red letters and red symbols. In FIG. 8A, prompt "CAL" 101 indicates the autorefractor has been switched "on." If calibration and self test is normal, screen FIG. 8B appears. In FIG. 8B, fixed illuminated circle 102 and prompt "Ready" indicate the instrument is properly working and ready to be used.

Figure 8C:
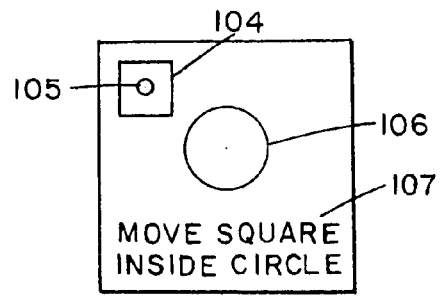

FIG. 8C shows that the operator has located the autorefractor in the proximity of an eye to be refracted. (An image of the eye being refracted ordinarily appears in screen FIG. 8C, omitted here for clarity.) With acquisition of an eye, an illuminated movable square 104 appears. Square 104 is centered on a reflection from the eye, First Purkinje Image 105. As the autorefractor moves relative to the eye, so does square 104 move. Also shown is fixed illuminated circle 106. Upon acquisition of an eye, illuminated circle 106 changes color to become illuminated yellow. Yellow indicates that square 104 should be moved inside circle 106. Prompt "Move Square Inside Circle!" 107, also indicates action to take.

Figure 8E:
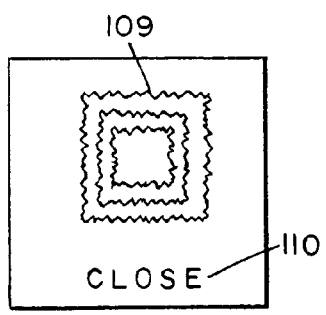
Figure 8D:
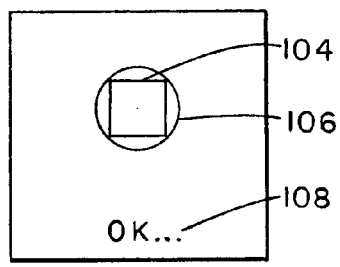

In FIG. 8D, movable square 104 has been moved inside fixed circle 106. Movable square 104 and fixed circle 106 now illuminate in green color, and brightly illuminate in a pulsed manner to indicate proper alignment and that the eye is being refracted. Prompt "OK . . . " 108 appears. This shows refraction is taking place. Because of an automatic eye tracking mechanism, as long as the autorefractor is located within a few millimeters of actual alignment, the instrument will continue automatically aligned. Time for completion of a measurement is a fraction of a second.

FIG. 8E shows an open-center large square 109 illuminated yellow and shimmering. This indicates, along with prompt "Close!" 110, that the autorefractor is too close to the eye and should be moved away from the eye. When the autorefractor is within the proper measurement distance from the eye, square 109 returns to its normal well-defined yellow lines, or, if located within fixed circle 106, to green illumination.

Figure 8F:
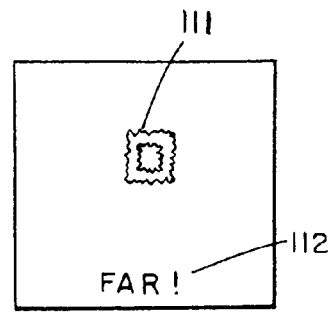

FIG. 8F shows a closed-center small square 111 illuminated yellow and shimmering. This indicates, along with prompt "Far!" 112, that autorefractor is too far from the eye and should be moved closer. When the autorefractor is within proper measurement distance from an eye being refracted, square 111 returns to its normal well-defined yellow lines, or, if located within fixed circle 106 of FIG. 8D, to green illumination.

Figure 8G:
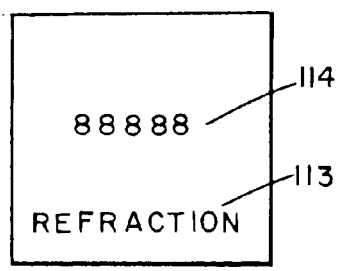

FIG. 8G shows prompt "Refraction" 113. Refractive measurement 114 (represented by marks) appears above prompt "Refraction" 113. At the touch of a switch, refractive measurement 114 is downloaded for printing, storage, or processing to prescription form. This allows accurate and speedy transmission of a prescription for corrective lenses and spectacles to an optical company.

A number of factors contribute to intuitive use. A first factor contributing to intuitive use, movable illuminated square 84 does not appear until the eye being acquired is within proper measurement range. The proper measurement range is relatively wide and somewhat insensitive to changes in vertex distance. This helps to initially acquire an eye. A second factor contributing to intuitive use, the image of an eye being refracted appears in screens 8C–D, and 8E–F, with illuminated guide marks superimposed. (For clarity, image of an eye being refracted is omitted.) An eye is enlarged a little over two times, comfortably fitting onto LCD screens FIGS. 8C–D. This helps to initially locate the instrument. A third factor contributing to intuitive use, the dimensions of movable square 104 and fixed circle 106 are approximately the size of an eye's iris as imaged on LCD screens FIGS. 8C–D. This further helps to locate the instrument in an intuitive manner. A fourth factor contributing to intuitive use, the objective of moving square 104 inside circle 106 is easily and intuitively understood. This, along with an automatic eye tracker for fine alignment adjustment, makes for exceedingly easy use.

FIGS. 9A and 9B show another preferred embodiment. This preferred embodiment differs from the first preferred embodiment in that this embodiment uses a simplified straight-line optical path. This embodiment also uses a plurality of optic fibers employed as staggered meridional photodetectors. In FIG. 9A, secondary source 39 on retina of eye 11 is generated by emitter 30 and lenses 31,34, via optical paths 32,41, and 21. Secondary source 39 exits through eye lens 40. Also shown are beam splitters 22, 33 and lens 42, meridional blockers 115 and 116, fiber optics bundles 115a and 117, and amplifiers 114. Additionally shown are first retinal image 50 and secondary retinal image 52. FIG. 9B shows near beam meridional plate 115 with representative meridian 119. Representative optic fiber 120 is one of a plurality of fibers distributed along meridian 119. FIG. 9B also shows far beam meridional plate 116 with representative meridian 119a and representative optic fiber 121. A minimum of three meridians are required to obtain full refractive measurements, as is well known to those skilled in the art. Representative optic fiber 120 is one of a plurality of fibers distributed along meridian 119. Meridians are equally spaced. Also shown are far beam meridional plate 116 with representative meridian 119*a* and representative optic fiber 121. Meridians of plates 115 and 116 are equally spaced and the meridians of each plate are staggered with respect to each other. Plates 115 and 116 may be fabricated of glass, plastic, or otherwise designed in a manner so that optic fibers are distributed along meridians as illustrated herein for the purposes of intercepting light energy along each meridian or each half meridian. Because meridians are staggered, measurements are interpolated for meridians intermediate to the staggered meridians. Light energy intensities so detected and measured enable calculation of full refraction of the eye.

FIGS. 10A–10D show yet another preferred embodiment. This preferred embodiment uses a simplified straight-line optical path, but this embodiment differs from the others in that it employs a spatial light modulator of constant illumination. Also, this embodiment, unlike those described earlier, instead of directly detecting changes in light intensities, detects diminution in light intensities. Diminution in light intensities is caused by opaque meridional blockers in the near beam path and in the far beam path. Further, diminution in light is detected by a single low-cost photodiode detector.

Spatial modulation is achieved by rotating a slot of light, pie-shaped, so that the rotating slot of light is imaged on the retina not as a point of light but as a rotating slot of light in the emmetropic eye. Spatial modulation may also be achieved by other means such as a micromirror or by alternately illuminating an array of emitters. Distance of a relay lens from an emitter pupil conjugate lens is fixed so that the slot of light is maximally in focus on the retina of an emmetropic eye. The rotating slot of light becomes the secondary source of light. Therefore, when blocker meridians coincide with the secondary source of light reflected from an eye, the reflected light is blocked from reaching a photodetector and the photodetector detects a minimum of light. Similarly, when blocker meridians are non-coincidental with the rotating slot of light of the secondary source because the slot of light has rotated to an angle where the blockers present an open space, then a maximum of light is detected by a photodetector.

It can be seen that the amount of light detected by a photodetector is dependent on the optical state of an eye, an emmetropic eye (normal vision) presenting the most contrast in light reflected out of the eye, and hyperopic and myopic eyes presenting different states, that is, the first retinal image as well as the second retinal image are accordingly shifted either nearer or farther away from a relay lens according to whether the eye is hyperopic (far sighted), emmetropic (normal) or myopic (near sighted). Therefore, blockers at two different distances detect differing amounts of light blocked and detected so that refractive states in various meridians are detected. These differing amounts of light correspond to $S_1$ and $S_2$ of previous embodiments. In this embodiment the first retinal image can be employed in place of the second retinal image, eliminated the detector pupil conjugate lens.

Frequency of detected light and frequency of signals from photodetector 133 depend on rotational speed of the slot of light. If the rotational speed is fixed, then the frequency of detected signals is fixed, and a bandpass filter 134 can be employed to pass only the desired signals of the fixed frequency and block all other signals.

In FIG. 10A, emitter 30 and emitter conjugate lens 31 via optical paths 32 and 21, using beam splitters 33 and 22, produce a secondary light source 122 on retina of eye 11. Secondary light source 122 exits eye 11 through eye lens 40 via optical path 21 and directed by beam splitter 34 to relay lens 34. Relay lens 34 produces first retinal image 50 and then, along optical path 41, impinges on detector conjugate lens 42, which produces second retinal image 52. Emitter 30 is mounted in transparent block 123 with rotor 124 mounted via axis 125 in block 123 and lens 31. Fiber optics plate 126 and representative optic fiber 127 sense position of rotor 124. Solid path optics 128 incorporates lens 42, near beam meridional blocker 129 and far beam meridional blocker 130. Blockers 129 and 130 are connected and aligned by axis rod 131. Rod 131 is preferably 1 mm (0.04 in) or less in diameter. Emitter 30 and rotor 124 via beam splitters 33 and 22, employing lenses 31,34, produce a secondary light source 122 on eye 11. Secondary light source 122 is returned from the eye via beam splitter 22 and along optical paths 21 and 41 through relay lens 34 and beam splitter 33. Relay lens 34 produces first retinal image 50. Detector pupil conjugate lens 42 then produces second retinal image 52. The light 132*a* is collected by light guide funnel 132 and directed onto a low-noise sensitive photodetector 133 such as the TAOS TSL 255 or TAOS TSL 257. Blockers 129 and 130 can be supported on their edges to eliminate rod 131. In a solid design, blockers 129 and 130 could be affixed to the block above of below. As shown in FIGS. 10A and 10D, rod 131 is used in the optional case of rotating the blockers and insures that both blockers rotate together equally.

The varying light 132*a* is caused by a spatial light modulator, that is, in this embodiment, the rotating light source of emitter 30 and rotor 124 being blocked in varying amounts. The amount blocked by any one meridian of blockers 129, 130, depends on position of retinal image 52. That is, the refraction of eye 11 corresponds to position of rotor 124 and corresponding meridians of blockers 129,130. Bandpass filter 134 detects only spatially modulated light from eye 11 created by a emitter 30 and rotor 124. Continuous light from the cornea and other non-varying sources is blocked. It can be seen that varying amounts of light 132 are used to detect intensities of light 122 from eye 11 so that meridional refractive powers can be calculated. Then, using these meridional refractive powers, measurements for full refraction of eye 11 can be calculated using, for example, Laurance's formula. Laurance's formula, well known to those skilled in the art, is $$M\Theta = C \cdot \sin^2\Theta \qquad [8]$$

where MΘ is the meridional power, in diopters, of a cylindrical lens of power C diopters measured at a meridianΘ degrees away from the axis of the cylinder.

FIG. 10B shows blockers 129 and 130, aligned and connected by axis rod 131. Representative meridian 135 is opaque to light. Transparent areas 136 are transparent to light. Meridians 135 occupy a total of 90 degrees of the circular area represented by blockers 129 or 130. Blocker 130 with transparent areas 138 has opaque representative meridians 137, which occupy 90 degrees. Meridians 137 of blockers 129,130, are equally spaced and staggered with respect to each other.

FIG. 10C shows alternative blockers 139 and 140 each with axis 131, transparent areas 141, and representative opaque half-meridians 142 and 143. Light emitter source 30 for half-meridians requires a half-meridian rotating light source, that is, rotor 124 has an aperture representing half of one meridian. Alternative blockers 139 and 140 can be substituted for blockers 129 and 130 respectively, as indicated by the related reference numerals in FIG. 10A.

FIG. 10D shows an end view of blockers 129 and 130 connected by axis rod 131. Frame 148 holds electromagnet 145, stop 149, and return spring 150. Magnetic lever 144 fixed to blockers 129,130 is moved by actuation of electromagnet 145. Motion of lever 144 is indicated by arrow 146. Corresponding meridional motion of blockers 129, 130 is indicated by arrow 147. Moving blockers 129,130, by a distance of one meridian eliminates the need to interpolate meridional measurements. Moreover, instead of measurements for three meridians, a total of six meridians are measured. Implementing the mechanism of FIG. 10D, however, does require one additional rotation of rotor 124. An additional rotation of rotor 124, however, requires only a fraction of a second.

In FIGS. 10A–10D, as will be appreciated by those skilled in the art, the a preferred embodiment can be implemented in numerous ways. For example, only one meridional blocker might be used, located at second retinal image 52, and emitter source moved plus and minus diopters. Similarly, arrangement of components can be changed to achieve the same results. Assumed throughout is that standard design practices such as employing stops, suppressing unwanted light, and so forth, be implemented in the actual embodiment. The embodiment described herein is meant as an example for illustrative purposes.

Figure 11A:
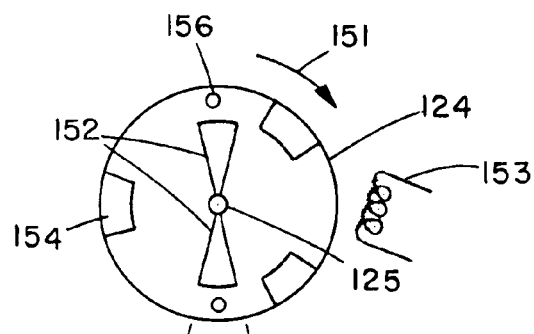
FIGS. 11A–11C show details of one embodiment of a spatial light modulator, which comprises a rotating aperture and rotor-position sensing optoelectronics.
Figure 11:
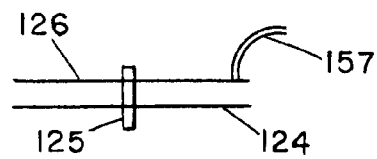
Figure 11C:
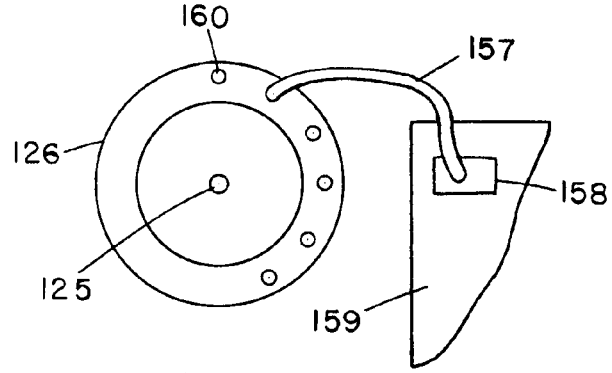
Figure 12:
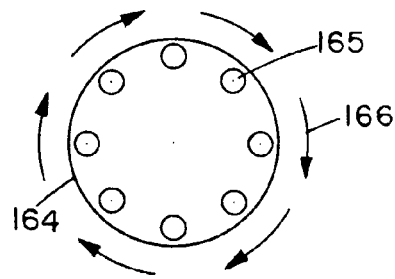

FIGS. 11A–11C show details of rotor 124 and rotor 124 position sensing elements. In FIG. 11A rotor 124 rotates around axis rod 131 as shown by arrow 151. Apertures 152 are width of one meridian 155. Representative magnets 154 and electromagnetic coils 153 cause rotor 124 to rotate. Rotor position holes 156 indicate position of meridional apertures 152. It is understood that emitter light impinges over the whole of rotor 124, including holes 156. FIG. 11-B shows a vertical view of rotor 124, axis rod 131, and optics fiber frame 126. Also shown is representative optic fiber 157. In FIG. 11-C, a plan view shows frame 126 and representative fiber holes 160. Fiber holes 160 are arranged in meridional fashion, that is, equally spaced and corresponding to positions of each meridian being measured. Representative fiber 157 senses light only when rotor 124 and rotor position holes are aligned. In FIG. 11-C, rotor position sensing amplifier 158 provides position sensing pulses to electronics 159 that provides timed pulses to driving coils 153, shown in FIG. 11A. Thus rotor 124 can be driven at a constant speed so that light 132a is of predetermine frequency to be passed by bandpass filter 134 yet blocking continuous light and all other frequencies.

Figure 12:
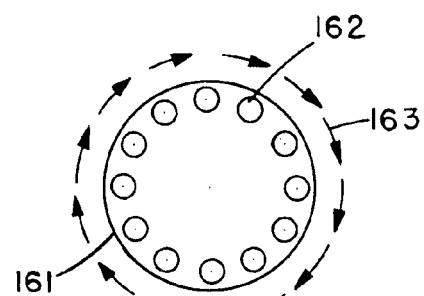
FIGS. 12A–12B show details of an alternate spatial light modulator employing in a single assembly LEDs that alternately illuminate in a serial manner while maintaining overall constant illumination.

FIG. 12A shows an alternative method of providing a varying light source. The embodiment of FIG. 12A comprises twelve emitter for six meridians. Representative light emitters 162 are arranged on circular mount 161 to provide illumination in series as indicated by arrows 163. FIG. 12B shows six emitters. This is shown by representative emitters 165 on mount 164. Emitters 165 illuminate one by one in a serial manner as indicated by arrows 166. The emitters 162 preferably turn on-off in a manner that results in unwanted continuous light being blocked, while the desired meridional signals are of a varying nature. One way to turn on and off emitters is in an overlapping saw-tooth manner. The overall light remains constant and continuous, while the desired meridional signal light varies according to the refraction of an eye being refracted. Thus one provides a spatially modulated light of constant illumination, yet use no moving parts. Having no moving parts has the advantage of simplicity and increased reliability. Care must be taken, of course, when fabricating the emitters in one integrated unit. Illumination can be in an overlapping sawtooth manner so that overall light illumination remains constant throughout the measurement cycle.

The invention described in these pages is monocular, battery powered, and entirely self contained, about the size of a standard ophthalmoscope, that is, pocket size. The basic refracting unit's compact and lightweight nature makes possible a variety of instruments such as a handheld binocular instrument. Such a binocular instrument can obtain refractions of both eyes and interpupillary distance (IPD) in one procedure. These three measurements are essential for prescribing corrective lenses and spectacles. Such a binocular instrument, when in an embodiment of about 80 in$^3$ (1310 cm$^3$) in size, compact and handheld, is eight times more capacious than a monocular autorefractor (about 10 in$^3$ [164 cm$^3$]). Much of this space is available for new functions. This includes a fundus camera to obtain images of the eye as well as electronics to analyze such images to aid disease detection and diagnosis as well as for internet connections.

Advantages are simplicity and extraordinarily low cost. This unique, affordable instrument will provide essential eye care to large populations in vast geographical regions. Thus one can summarize advantages as including methods to obtain full refraction spherocylinder measurements; extreme simplicity of embodiment, with only a total of only four lenses, including the illumination and imaging section; a minimal number of components: Only two lenses for the detector path and only one CCD detector; or only two lenses for the detector and only one photodiode detector; being very simple to form a secondary light source on the retina: and use of a beam splitter to incorporate one emitter with one lens.

Also significant is the use of solid-path optics with most of the discrete optical components being integrated into one solid-path optical block, which eliminates many discrete components, boosts ruggedness, increases reliability, cuts weight, decreases and reduces cost. Solid-path optics also means greater compactness. Optical path length is shortened by the reciprocal of the index of refraction. Using a material with an index of refraction of 1.6 means the optical path length is reduced by about 40%.

Use of a basic autorefractor provides complete spherocylinder measurements, and also creates an instrument incorporating additional capabilities, such as keratometry and inclusion of a pupillometer and eye camera. The invention is of assistance to the user in diagnosing eye diseases. The pupillometer assists in diagnosing neurological conditions such as head trauma. Design of the instrument facilitates easy incorporation of a keratometer to measure curvature of the cornea.

The device of the invention is conveniently of pocket size, battery powered, and entirely self-contained for high portability. It is easy to use: lightweight, small, and similar to use of a standard ophthalmoscope.

Although the description above contains many specifications, these should not be construed as limiting the scope of the invention but as merely providing illustrations of some of the presently preferred embodiments of our invention. For example, lenses may be of glass or plastic and may be of complex or simple design, arrangement of components and configurations may vary, etc. Thus the scope of the invention should be determined by the appended claims and their legal equivalents, rather than by the examples given.

The inventory claimed is:

1. Apparatus for obtaining spherocylinder measurement of an eye comprising:
   a primary emitter of a light beam imaged by optical elements to form a secondary retinal light source from said light beam on said eye's retina;
   a photodetector comprising a light detector for measurement of at least a first retinal image and a second retinal image of said secondary retinal light source as observed by said photodetector respectively at proximal and distal positions relative to said secondary retinal light source and generation of signals proportional to the measured images said photodetector being positioned,
   optically beyond said first retinal image in a near beam to detect diminutions of light in various meridians of said near beam, and
   optically beyond said second retinal image in a far beam to detect diminutions of light in various meridians of said far beam,
   wherein all elements of the detector system are in a straight line optical path, and
   computation means responsive to said signals for calculating said spherocylinder measurement of said eye.

2. Apparatus for obtaining spherocylinder measurement of an eye as in claim 1, wherein said photodetector further comprises a detector pupil conjugate lens.

3. Apparatus for obtaining spherocylinder measurement of an eye as in claim 1, wherein said photodetector further comprises a beam splitter and a mirror assembly.

4. Apparatus for obtaining spherocylinder measurement of an eye as in claim 1 wherein said photodetector further comprises an array of light detectors spatially arranged to detect light at said distal position in various meridians of a far beam and an array of light detectors spatially arranged to detect light at said proximal position in various meridians of a near beam.

5. Apparatus for obtaining spherocylinder measurement of an eye as in claim 4,
   wherein said diminutions of light in various meridians of said far and near beams are caused by staggered opaque meridians;
   whereby in response to said diminutions of light said photodetector generates said signals for calculating said spherocylinder measurement of said eye.

6. Apparatus for obtaining spherocylinder measurement of an eye as in claim 4 wherein said arrays of light detectors disposed in both said distal and proximal positions are arranged in rows such that light signals from parallel rows in the first and second retinal images may be summed and compared to find meridional power at right angles to the rows and further comprising there being a sufficient number of parallel rows at different angular orientations to allow the complete spherocylinder power of the eye to be determined.

7. Apparatus for obtaining spherocylinder measurement of an eye as in claim 1, further comprising:
   said primary emitter being spatially modulated;
   said diminutions of light in various meridians in said far and near beams being caused by staggered opaque meridians; whereby in response to said diminutions of light said photodetector generates signals for calculating said spherocylinder measurement of said eye.

8. Apparatus for obtaining spherocylinder measurement of an eye as in claim 1 further comprising:
   said lenses causing light beam from said emitter to be focused at optical infinity;
   said light beam being directed via a beam splitter to a cornea of said eye such that said cornea produces a reflection showing optical center of said eye;
   said reflection being returned to said lens and therethrough to said beam splitter directed to said photodetector, said photodetector located at such distance from said lens so that said reflection from said eye is in focus on said photodetector;
   whereby said signal generated in response thereto by said photodetector further indicates location of said reflection and said optical center of said eye thus facilitating alignment of said eye with optics of an optical instrument.

9. Apparatus for obtaining spherocylinder measurement of an eye as in claim 1 wherein said photodetector comprises a CCD photodetector or a photodiode.

10. Apparatus for obtaining spherocylinder measurement of an eye as in claim 1, wherein said primary emitter comprises a laser diode emitter producing a narrow beam in conjunction with a beam splitter, whereby sharpness of said secondary retinal light source on said retina is enhanced.

11. Apparatus for obtaining spherocylinder measurement of an eye as in claim 5, further comprising said straight-line optical path comprising at least one block of transparent material employing air spaces, whereby reflection, transmission, and refraction of an impinging light beam is caused by appropriately shaped air spaces of said block.

12. Apparatus for obtaining spherocylinder measurement of an eye as in claim 11, further comprising a plurality of blocks of transparent material fixed together to form a single composite block, whereby shaped interfaces at the junctions between adjacent blocks cause refraction of an incident light beam.

13. Apparatus for obtaining spherocylinder measurement of an eye as in claim 1, further comprising an illuminated pinhole cooperative with an emitter, beam splitters and lenses for locating the optical center of an eye, such together forming a compact apparatus to track said optical center of said eye while causing relaxation of said eye's accommodation.

14. Apparatus for obtaining spherocylinder measurement of an eye as in claim 9, further comprising at least two color emitters emitting light beams at different wavelengths from each other, said emitters illuminated alternately and emitting at infrared wavelengths such that said retina and other structures of said eye are imaged in infrared light, and said detector comprising a black and white CCD, whereby visible color imaging of an eye's retina can be achieved using said black and white CCD.

15. Apparatus for obtaining spherocylinder measurement of an eye as in claim 9, further comprising means for collection of light for said photodiode, said means comprising a cone-shaped optical guide, whereby said photodiode active area may be of small dimensions.

16. Apparatus for obtaining spherocylinder measurement of an eye as in claim 4, wherein light sensitive elements of said arrays comprise light sensitive plates, said plates generating electrical signals when impinged on by a light beam.

17. Apparatus for obtaining spherocylinder measurement of an eye as in claim 5, further comprising means for angularly rotating opaque blockers, whereby the number of measured meridians is multiplied.

18. Apparatus for obtaining spherocylinder measurement of an eye as in claim 7, wherein spatial modulation comprises dispositions of a rotating aperture, which said aperture is a rotor of a motor, in cooperation with said emitter.

19. Apparatus for obtaining spherocylinder measurement of an eye as in claim 7, wherein spatial modulating comprises disposing multiple emitters illuminated sequentially, whereby modulation is achieved with no moving parts.

20. Apparatus for obtaining spherocylinder measurement of an eye as in claim 7, wherein said detector of diminution of light comprises optical blockers inserted in a solid block of transparent material, whereby alignment of said blockers is fixed.

21. Apparatus for obtaining spherocylinder measurement of an eye as in claim 20, wherein said optical blockers are arranged in a straight path, whereby the number of optical elements is minimized.

22. Apparatus for obtaining spherocylinder measurement of an eye as in claim 8, wherein said optical instrument for facilitation of alignment of said eye comprises a screen to visibly show location of said optical center of said eye, said optical instrument further being manually moveable to achieve optical alignment between said eye and said instrument.

23. Apparatus for obtaining spherocylinder measurement of an eye as in claim 22, wherein means for manually moving said instruments comprises a tiltable plate, whereby tilting of said plate allows steering of an emitter beam and provides optical alignment between said eye and said instrument.

24. Apparatus for obtaining spherocylinder measurement of an eye as in claim 23, wherein said tiltable plate and a moveable beam splitter are disposed such that movement of said beam splitter in an axis parallel to beam direction and tilting of said plate in a second axis allows steering of an emitter beam in two axes and provides optical alignment between said eye and said instrument.

25. Apparatus for obtaining spherocylinder measurement of an eye as in claim 22, wherein said screen on which said reflection from said eye visibly appears is formed a first geometric figure, which said first geometric figure can be fitted onto a second geometric figure also formed on said screen, whereby said second geometric figure represents the optical center of said optical instrument and said first geometric figure represents the optical center of said eye, and coincidence thereof on said screen indicates achievement of optical alignment between said eye and said instrument.

26. Apparatus for obtaining spherocylinder measurement of an eye as in claim 22, wherein on said screen an image of said eye and an image of said reflection produced by said eye appear, and superimposition of said reflection from said eye on said image of said eye indicates achievement of optical alignment between said eye and said instrument.

27. Apparatus for obtaining spherocylinder measurement of an eye as in claim 26, wherein a color geometric figure formed on said screen represents said reflection produced by said eye.

28. Apparatus for obtaining spherocylinder measurement of an eye as in claim 26 further comprising indicia formed on said screen instructing a user how to move said instrument to obtain said superposition.

29. Apparatus for obtaining spherocylinder measurement of an eye as in claim 26 further comprising geometric figures in motion on said screen indicate spatial location of said instrument.

30. A method for obtaining spherocylinder measurement of an eye comprising:
    creating an optical light path by causing a primary emitter of a light beam imaged by optical elements to form a secondary retinal light source from said light beam on said eye's retina;
    disposing a photodetector comprising a light detector in said optical light path for measurement of at least a first retinal image and a second retinal image of said secondary retina light source as observed by said photodetector respectively at proximal and distal positions relative to said secondary retinal light source and generation of signals proportional to the measured images said photodetector being positioned,
    optically beyond said first retinal image in a near beam to detect diminutions of light in various meridians of said near beam, and
    optically beyond said second retinal image in a far beam to detect diminutions of light in various meridians of said far beam,
    wherein all elements of the detector system are in a straight line optical path, and
    calculating from said signals said spherocylinder measurement of said eye.

31. A method for obtaining spherocylinder measurement of an eye as in claim 30 wherein optical properties of said eye modify and direct light rays in said optical light path such that the luminous irradiance comprising pixels impinging on said photodetector varies in response to said optical properties of said eye.

32. A method for obtaining spherocylinder measurement of an eye as in claim 31 further comprising from said measurement determining a correct prescription for the adjustment of said eye to emmetropic vision.

33. A method for obtaining spherocylinder measurements of an eye as in claim 31 further comprising disposing in said optical path two photodetectors and wherein said optical properties of said eye modify and direct light rays in said optical light path such that the luminous irradiance comprising pixels impinging on said two photodetectors varies in response to said optical properties of said eye.

34. A method for obtaining spherocylinder measurement of an eye as in claim 33 further comprising from said measurement determining a correct prescription for the adjustment of said eye to emmetropic vision.

35. A method for obtaining spherocylinder measurements of an eye as in claim 31 further comprising disposing in said optical path a beam splitter and a mirror assembly and wherein said optical properties of said eye modify and direct light rays in said optical light path such that the luminous irradiance comprising pixels impinging on said photodetector varies in response to said optical properties of said eye.

36. A method for obtaining spherocylinder measurement of an eye as in claim 35 further comprising from said measurement determining a correct prescription for the adjustment of said eye to emmetropic vision.

37. A method for obtaining spherocylinder measurement of an eye as in claim 30 further comprising spatially modulating said light beam.

38. A method for obtaining spherocylinder measurement of an eye as in claim 37 further comprising from said measurement determining a correct prescription for the adjustment of said eye to emmetropic vision.

39. A method for obtaining spherocylinder measurement of an eye as in claim 30 further comprising disposing as part of said photodetector a detector pupil conjugate lens.

40. A method for obtaining spherocylinder measurement of an eye as in claim 30 further comprising disposing as part of said photodetector a beam splitter and a mirror assembly.

* * * * *